| (12) | United States Patent | (10) Patent No.: US 10,509,000 B2 |
|---|---|---|
| | He et al. | (45) Date of Patent: Dec. 17, 2019 |

(54) X-RAY FLUORESCENCE DEVICE CALIBRATION

(71) Applicant: Tribogenics, Inc., Los Angeles, CA (US)

(72) Inventors: Tianqing He, Los Angeles, CA (US); Carlos Camara, Los Angeles, CA (US); Mark G. Valentine, Los Angeles, CA (US); Dan Cuadra, Los Angeles, CA (US); Eric W. Wong, Los Angeles, CA (US); German Om, Los Angeles, CA (US); Andy Kotowski, Los Angeles, CA (US); Justen Harper, Los Angeles, CA (US)

(73) Assignee: Tribo Labs, Marina del Rey ( * ) Notice: Subject to any disclaimer, the term of this patent is extended or adjusted under 35 U.S.C. 154(b) by 211 days.

(21) Appl. No.: 15/159,722

(22) Filed: May 19, 2016

(65) Prior Publication Data

US 2016/0341677 A1 Nov. 24, 2016

Related U.S. Application Data

(60) Provisional application No. 62/164,426, filed on May 20, 2015.

(51) Int. Cl.
*G01N 23/223* (2006.01)

(52) U.S. Cl.
CPC ..... *G01N 23/223* (2013.01); *G01N 2223/076* (2013.01); *G01N 2223/301* (2013.01); *G01N 2223/303* (2013.01)

(58) Field of Classification Search
CPC ................. G01N 23/00; G01N 23/223; G01N 2223/303; G21K 1/02; A61B 6/06
USPC ........................... 378/44, 160, 162, 165, 207
See application file for complete search history.

(56) References Cited

U.S. PATENT DOCUMENTS

| 4,362,935 | A | 12/1982 | Clark, III |
|---|---|---|---|
| 6,486,573 | B2 | 11/2002 | Yagi et al. |
| 2008/0152079 | A1 | 6/2008 | Tannian et al. |
| 2011/0142200 | A1 | 6/2011 | Piorek et al. |

FOREIGN PATENT DOCUMENTS

WO    WO 2004/052059 A2    6/2004

OTHER PUBLICATIONS

International Search Report on related PCT Application No. PCT/US2016/033361 from International Searching Authority (KIPO) dated Sep. 1, 2016.
Written Opinion on related PCT Application No. PCT/US2016/033361 from International Searching Authority (KIPO) dated Sep. 1, 2016.

*Primary Examiner* — Jurie Yun
(74) *Attorney, Agent, or Firm* — Klein, O'Neill & Singh, LLP

(57) ABSTRACT

A handheld XRF device having a shutter including a calibration material. An automatic calibration sequence may be performed with the shutter in the closed position.

12 Claims, 5 Drawing Sheets

X-RAY FLUORESCENCE DEVICE CALIBRATION

CROSS REFERENCE TO RELATED APPLICATIONS

This application claims the benefit of the filing date of U.S. Provisional Patent Application No. 62/164,426, filed on May 20, 2015, the disclosure of which is incorporated by reference herein.

BACKGROUND OF THE INVENTION

The present invention relates generally to x-ray fluorescence (XRF) devices, and more particularly to calibration of handheld XRF devices.

XRF devices are often used to determine composition of materials. In general, XRF devices generate x-rays to strike a sample, sense return radiation from the sample using a sensor, and analyze the sensed return radiation from the sample to determine material composition of the sample. Conveniently, handheld XRF devices are available for use in the field, providing mobility while identifying materials of interest.

Unfortunately, as with any device that is long in the field, capabilities of XRF devices long deployed in the field may suffer degradation over time, particularly if the devices are not regularly returned to a depot for servicing and maintenance. Degradation may occur in several forms, but degradation, in whole or in part, of accuracy and/or precision of results of use of XRF devices may be particularly undesirable.

BRIEF SUMMARY OF THE INVENTION

Aspects of the invention relate to calibration of XRF devices. Some aspects of the invention provide a handheld XRF device with a shutter used in calibration of the XRF device. In some embodiments the shutter is internal to a housing of the XRF device, with the housing for example also housing an x-ray generator of the XRF device. In some embodiments the shutter is of, or includes, material, which may be used for calibration purposes. In this regard the material may be considered calibration material. In some embodiments the calibration material is a particular element. In some embodiments the calibration material is a particular alloy. In some embodiments the calibration material includes a plurality of elements and/or a plurality of alloys. In some embodiments the elements and/or alloys are embedded in, or are interlaid by, a matrix of other material. In some embodiments the calibration material is an epoxy mixture including, or which has embedded therein, several elements. In some embodiments the several elements, when struck by x-rays, provide a return signal with particular desired intensities or amplitudes, at particular desired wavelengths for a particular x-ray excitation spectra.

In some aspects, an exemplary embodiment of the invention provides a method of calibrating a device, comprising: generating x-rays from an x-ray generator within a housing; receiving a return signal emitted by a material struck by the x-rays in a sensor, the material being of a shutter within the housing; providing data generated by the sensor to electronics connected to the x-ray generator and the sensor; processing the data in the electronics; wherein the electronics comprise at least one processor, and the data from the sensor comprises wavelengths of a set of peak magnitudes of a return spectrum, and the at least one processor compares the wavelengths of the set of peak magnitudes of the return spectrum with a set of expected wavelengths of peak magnitudes of a return spectrum, and updates parameter relating to the operation of the x-ray generator and sensor based on the analysis of the comparison of the wavelengths of the set of peak magnitudes of the return spectrum with a set of expected wavelengths of peak magnitudes of a return spectrum.

In some aspects, an exemplary embodiment of the invention provides a handheld x-ray fluorescence (XRF) device, comprising: an x-ray generator for generating x-rays, the x-ray generator located within a housing, the housing having at least one window for the x-rays to pass through; a sensor for detecting a return signal emitted by a calibration material struck by the x-rays; a shutter movable relative to the x-ray generator between an open position not occluding the window to and a closed position occluding the window, the shutter comprised of a calibration material; and electronics for processing data generated by the sensor, the electronics comprising at least one processor, the at least one processor configured for comparing the data from the sensor to a known data set associated with the calibration material stored in a memory.

These and other aspects of the invention are more fully comprehended upon review of this disclosure.

DETAILED DESCRIPTION

Figure 1:
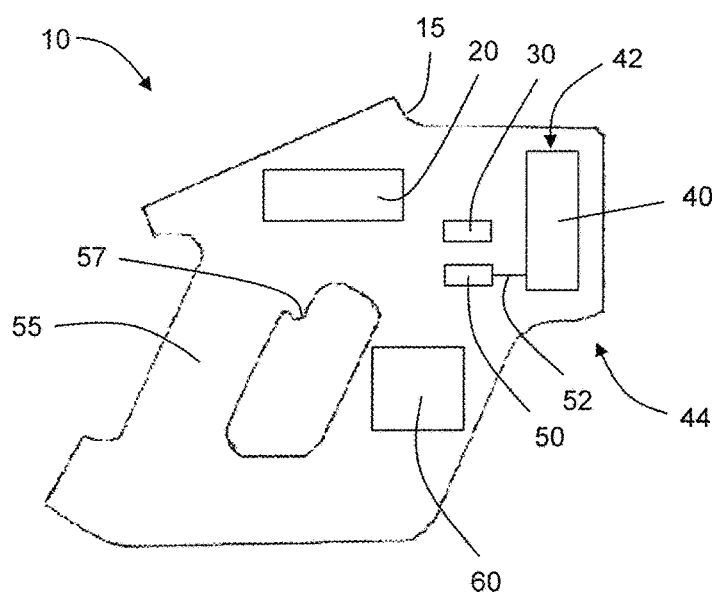
FIG. 1 shows a semi-schematic semi-block diagram side cross sectional view of a handheld x-ray fluorescence (XRF) device in accordance with aspects of the invention.

FIG. 1 shows a semi-schematic semi-block diagram side cross sectional view of a handheld x-ray fluorescence device 10 in accordance with aspects of the invention. The x-ray fluorescence device comprises a housing 15 with an x-ray generator 20, a sensor 30, a shutter 40, and a drive motor 50 to move the shutter within the housing. Electronics 60 to operate components of the device and perform processing of information is also shown as within the housing although in various embodiments some of the electronics may be external to the housing, or the device for that matter. In the device of FIG. 1, the housing forms a grip 55 for an operator with a control 57 proximate the grip to operate the device. The grip is generally shaped to fit an operator's hand (not shown).

The housing 15 is generally shaped for ease in pointing the device 10 at a target (not shown) to be scanned. The housing is large enough to accommodate all the required components, and at the same time compact enough to be easily portable. The housing may be made from any material that is sufficiently light weight and durable, for example plastic, composites, aluminum, and lightweight metal alloys. In most embodiments the housing is substantially opaque to x-rays, other than one or more windows in the housing, for example as discussed below.

The x-ray generator 20 is located in the housing 15 near a front 44 of the housing, such that the x-rays generated by the x-ray generator may pass through a window (not shown) in the housing, with the window generally transparent to x-rays. The x-ray generator generates x-rays. In some embodiments the x-ray generator generates x-rays with a specific x-ray excitation spectra. Unless indicated by the context, in this application the term "front" is used to mean the part or parts of the device from which x-rays are emitted. The sensor 30 is also located near the front of the housing and is aligned with the window, or a second window in some embodiments (not shown) such that the sensor will be able to capture high energy radiation, for example x-rays reflected back from a target surface or material (not shown) to the device 10.

The shutter 40 is located in a space 42 between the front 44 of the housing 15 and the x-ray generator 20 and sensor 30. The shutter is sized to occlude both the window, and, if present, the second window, which are located on the front of the housing, as will be discussed in more detail below with reference to FIGS. 2 and 3. The shutter is connected to the drive motor 50 by a drive element 52. The connection between the shutter and the drive element may be made mechanically, such as through a threaded connection, where the drive element has male threads formed on an end, and the shutter has corresponding female threads formed in a bore through the shutter, or the drive element and shutter may be connected by the use of an external fastener or fasteners, such as a nut or nuts threaded on male threads formed on the drive element. The connection may also be made through the use of an adhesive, or the parts may be welded where their respective materials permit.

The shutter is made from, or includes, a material that may be used in a calibration process, and the material may therefore be considered a calibration material. In some embodiments the calibration material may be a uniform material, or a composite. The composites may be in various forms. The forms can include both contiguous and non-contiguous parts. The structure and composition of various embodiments of the calibration material are discussed in detail below.

The electronics 60 connect various of the components and further provide processing of data received by the sensor 30. Based on the data received by the sensor and programming in the electronics 60 or based on other input, for example, data input from external sources, for example, by an operator (not shown), the electronics 60 can control various parameters and functions of the x-ray generator 20, sensor, the operation of the drive motor 50 and power on and off of the device 10. Based on operator input, the electronics can also signal the x-ray generator, sensor, and drive motor to perform a calibration of the device. The electronics may also automatically cause the device to perform a calibration if the analysis of the data from a first calibration results in the electronics making changes to parameters or functions of the x-ray generator, sensor, or drive motor.

Figures 2, 3:
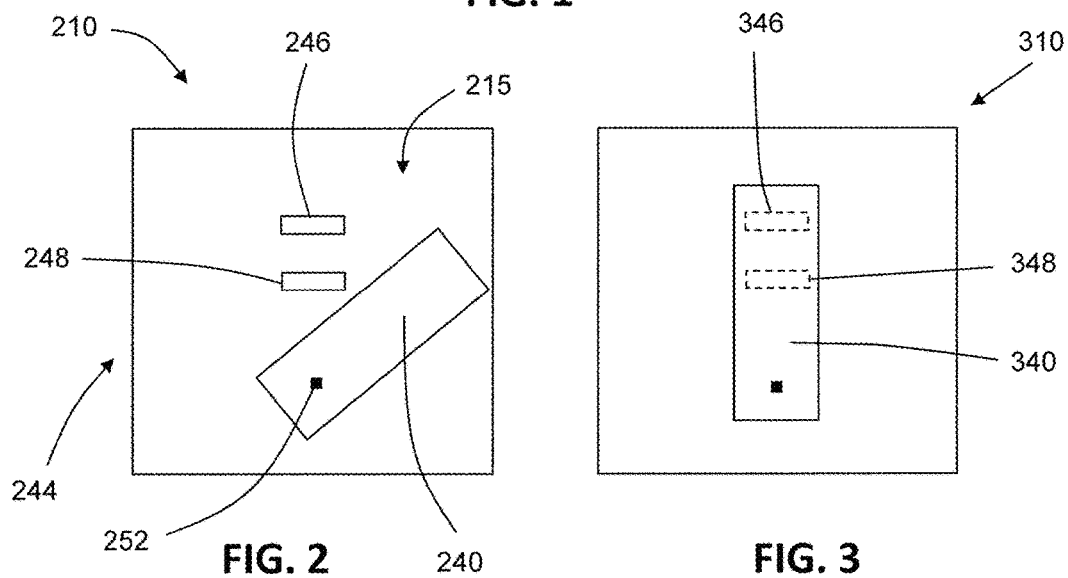
FIG. 2 is a plan view of a portion of the front of the XRF device of FIG. 1.
FIG. 3 is a further plan view of a portion of the front of the XRF device of FIG. 1.

FIG. 2 is a plan view of a portion of the front 244 of the device 210. As shown in FIG. 2, the shutter 240 has been rotated aside, for example, by operation of the drive motor, and the first aperture 246 and the second aperture 248 are unobstructed. In this position, the x-ray generator may operate to send x-rays through the first aperture to a target (not shown), and the sensor may receive the x-rays returned from the target through the second aperture. The drive motor (not shown) is connected to the shutter by the drive element 252. In this embodiment, the shutter has been rotated clockwise. However, in other embodiments the shutter rotates counter-clockwise, and still other embodiments the shutter has an operator selectable direction of motion. In still other embodiments the shutter is omitted entirely. In these embodiments, a component of calibration material that is separate from the device, but can be inserted through, for example, a slot in the top or bottom of the housing 215 to occlude the window and, if present the second window, in order to perform the calibration. In still other embodiments, the shutter may also be used in combination with another component for calibration, such that the component provides the calibration material, and the shutter serves only to prevent the emission of x-rays from the device. In some embodiments, the shutter may be external to the device. These embodiments have the advantage of being able to change the shutter when the shutter provides the calibration material more easily than embodiments with a shutter/calibration material combination internal to the housing. The shutter or component of calibration material can be made from a specific alloy or from a combination of pieces, each composed of a different element compound or alloy, or a combination thereof as discussed in detail below.

FIG. 3 is a plan view of a portion of the front of the device 310. As shown in FIG. 3, the shutter 340 has been rotated, for example, by operation of the drive motor, to a center, storage, or calibration position that occludes both the window 346 and the second window 348. The drive motor (not shown) rotates the shutter in a direction opposite that which moved the shutter clear of the window and second window, moving the shutter from the operational configuration shown in FIG. 2, to the storage or calibration configuration shown here. In this position, the occlusion of the window, and when present, the second window, by the shutter prevents the x-ray generator (not shown) from transmitting x-rays external to the device, and the shutter also prevents the sensor (not shown) from receiving high energy radiation, for example, x-rays generated or reflected from objects external to the device. In some embodiments, the drive motor and drive element are mounted below the window and, when present, the second window. However, other placements for the drive motor, drive element, and shutter are contemplated, including anywhere around the general perimeter of the window and, when present, the second window. The only requirement for placement is that the drive motor and drive element be able to move the shutter in to and out of occlusion of the window and, when present, the second window.

Figure 4:
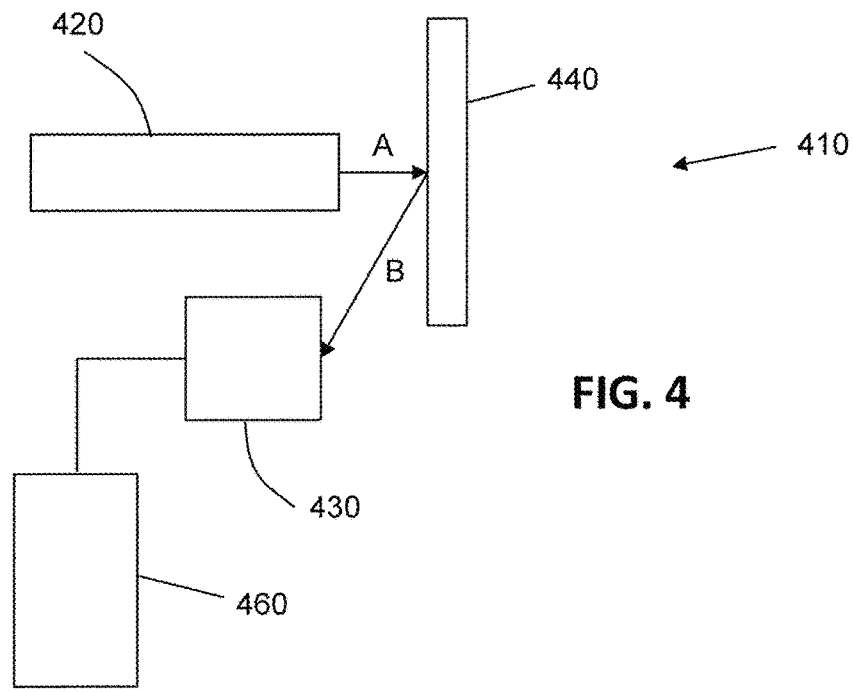
FIG. 4 shows a semi-schematic semi-block diagram view of components of the XRF device of FIG. 1 with respect to a calibration operation in accordance with aspects of the invention.

FIG. 4 shows a semi-schematic semi-block diagram view of some of the components of device 410, which may be a device such as discussed with FIGS. 1-3 or any of them, which are discussed in the context of a calibration sequence. As shown in FIG. 4, a shutter 440 may also serve as a calibration target for the device 410. In this embodiment, the shutter comprises a calibration material. When the device 410 is in the storage or calibration configuration shown in FIG. 3, the shutter is located between an x-ray generator 420 and the window. Likewise, the shutter is located between the sensor 430 and a window, or if one is present, a second window. Because the shutter is directly in front of both the x-ray generator and sensor, and because its material composition can be chosen at the time of manufacture from materials with well-known x-ray fluorescence properties as discussed is more detail below, the shutter makes an optimal or near optimal calibration target for the device. Further, the material for the shutter can be chosen such that it contains multiple elements so that their corresponding XRF intensity can be used to monitor changes in energy-spectrum of the X-ray source used for excitation.

In some embodiments, when an operator (not shown) uses the control, the control initiates a calibration sequence in the device 410. The x-ray generator 420 begins emitting x-rays which are shown schematically in FIG. 4 by the arrow labelled "A." In various embodiments the x-rays have a specific x-ray excitation spectra, based for example on characteristics of the x-ray generator. These x-rays strike the shutter 440, which, as stated above, is a material of known composition. The shutter emits a return signal in response to being struck by the x-rays, and at least some of the return signal, shown schematically by the arrow labelled "B," is received by the sensor 430. The data generated in the sensor from the receipt of the return signal is then passed through a wired or wireless path, or a combination thereof, to electronics 460 for processing. In processing, the electronics compares the data generated from the receipt of the return signal by the sensor to a known data set based on the material composition of the shutter 440. Based on an analysis of the comparison, the electronics may then adjust any of a number of parameters of the functions of the various components. In some embodiments, after these adjustments are made, a second calibration sequence is performed to verify that the device 410 is calibrated. Once the electronics determine that the device is calibrated, in some embodiments the electronics notify the operator. Notification may be made by lighting a certain color light emitting diode (LED) (not shown) that is placed in an opening (not shown) on the housing 415, or by displaying a message on a screen (not shown), or by emitting an audible tone, or any number of other ways. This calibration may lead to more accurate measurements.

Figure 5:
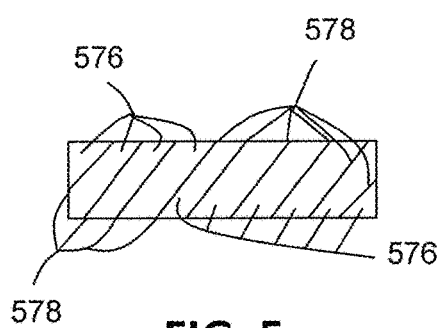
FIG. 5 illustrates aspects of a calibration material in accordance with aspects of the invention.

As shown in FIG. 5, one embodiment of the calibration material may be a uniform material. The uniform material 540 can be selected for inherent properties such as the material's response to x-ray excitation, and specifically, the spectrum produced by the material when the material is excited by x-rays. To manufacture the calibration material, which may be used as a shutter, strips of the uniform material are formed, and then cross cut to create individual pieces of calibration material for use in the device (not shown). As described above, the calibration material may or may not be used as a shutter 40 (FIG. 1).

Figure 6:
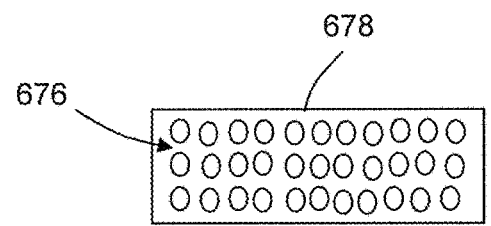
FIG. 6 illustrates aspects of a further calibration material in accordance with aspects of the invention.

FIG. 6 shows an alternative embodiment of the calibration material. Multi-filament ropes 676 are arranged in a matrix 678 to provide a uniform, but non-contiguous material. In some embodiments the matrix is an epoxy or epoxy like material. Each multi-filament rope may be of the same composition, or there may be two or more compositions arranged in a pattern in the matrix. This construction of multi-filament ropes in a matrix allows materials that have the desired physical properties but can best be manipulated as filaments to still be used in a component that has a requirement to occlude a window or a plurality of windows. As with the uniform material of FIG. 5, the matrix containing the multi-filament ropes is formed in long strips and then may be cross cut to form the individual calibration material components. The multi-filament ropes are discussed in more detail in relation to FIG. 7.

It is preferable that the matrix does not produce XRF spectral lines in the region of interest. An example of a suitable matrix that does not produce XRF interference would be a polymer composed of light elements such as C, N, O, S or P. However, elements lighter than Ca are suitable. The matrix could also contain heavier elements if their XRF lines do not overlap with the active elements. A heavier element can also be used if its XRF lines are used for the calibration.

Figure 7:
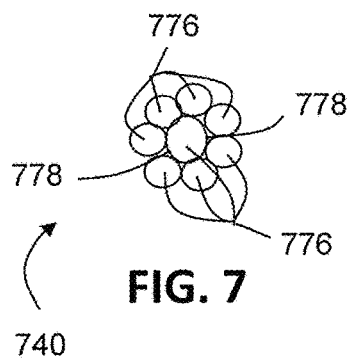
FIG. 7 illustrates aspects of portions of the calibration material of FIG. 6.

FIG. 7 shows a detail view of an individual multi-filament rope of FIG. 6. The multi-filament rope 740 is formed from individual strands 776, each of a different element, compound or alloy. Multiple strands within the rope can be made of the same material composition, a different material composition, or individual strands may themselves be formed from smaller individual strands. While the embodiment shown in FIG. 7 has seven strands wound around a central eighth strand, other embodiments may have any number of strands, and may or may not have a central strand around which other strands are wound. Individual strands may vary in size depending on the precise material used. For example, when a central strand is present, the central strand may be larger than the strands wound around it or vice versa. Some individual strands in the winding, with or without a central strand may be larger than the others. The physical composition of the strands may be wholly driven by the requirement to produce a spectrum that will allow a proper calibration of the device. The rope may be reinforced by embedding the rope in a matrix, such as a polymer as shown in FIG. 6.

Figure 8:
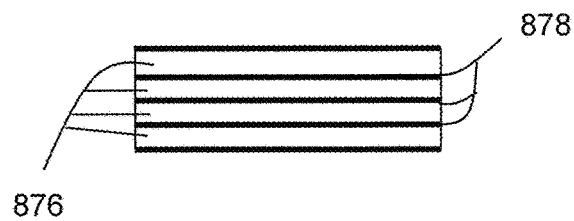
FIG. 8 illustrates aspects of a further calibration material in accordance with aspects of the invention.

As shown in FIG. 8, another embodiment of the calibration material may be a laminate composed of different metals, compounds and/or alloys. The layers 876 of the laminate may be oriented in any number of directions, such as on the diagonal, vertical, or they layers 876 may be oriented horizontally as shown in FIG. 8, or in any direction including vertical, horizontal or anywhere in between. The laminate may also include layers that run in different directions. The individual layers within the laminate could be of the same material composition, or they could be different, they could have some materials that comprise multiple different layers within the laminate. The laminate may be reinforced by embedding in a matrix 878, such as a polymer. As with the uniform material of FIG. 5, individual calibration samples can be made by cutting cross-sections from the laminate so that each face of the cross-sections shows a uniform distribution of the various elements.

Figure 9:
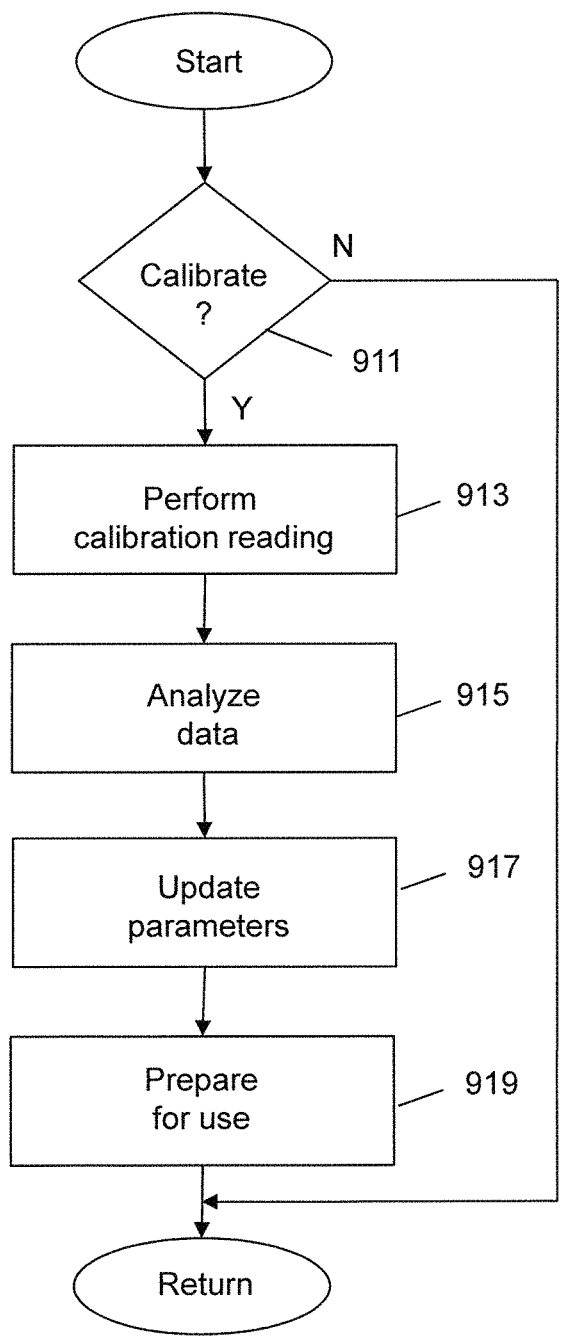
FIG. 9 is a flow diagram of a process of operating an XRF device with a calibration feature in accordance with aspects of the invention.

FIG. 9 is a flow diagram of a process of operating an XRF device with a calibration feature. The process of FIG. 9 may, for example, be performed by the device of FIG. 1, and portions of the process of FIG. 1 may be performed by electronic circuitry of the device of FIG. 1, or such electronic circuitry and electronic circuitry external to the device of FIG. 1 but in communication with the electronic circuitry of the device of FIG. 1. In some embodiments the electronic circuitry, internal and/or external to the device of FIG. 1, may comprise a processor configured by program instructions.

In block 911 the process determines if a calibration is to be performed for an XRF device. In some embodiments the calibration is performed every time the XRF device is powered on. In some embodiments the calibration is performed after the XRF device is powered on a plurality times. For example, the calibration may be performed every fifth time the XRF device is powered on. In some embodiments the calibration is performed after a predetermined number of activations of the XRF device. In some embodiments the calibration is performed based on a command or request for a calibration from a user, for example using an input device of the XRF device or an input device of another device in communication with the XRF device.

In block 913 the process performs a calibration reading. In some embodiments the process performs a calibration reading by generating x-rays by an x-ray generator of the XRF device, with the x-rays striking a calibration material and sensing a return spectrum, or portion of spectrum, from the calibration material. In some embodiments the calibration material is within a housing of the XRF device. In some embodiments the calibration material is of a shutter of the XRF device. In some embodiments the shutter is internal to the XRF device. In some embodiments the process, as part of performing the calibration reading, closes the shutter prior to generation of x-rays. In some embodiments the process determines if the shutter is closed, and closes the shutter if not closed, prior to generating the x-rays.

In block 915 the process analyzes information of the sensed return spectrum. In some embodiments a processor of the XRF device analyzes the information of the sensed return spectrum in accordance with program instructions. In some embodiments a processor of a device in communication with the XRF device performs the analysis. In some embodiments the process compares wavelengths of expected peak magnitudes with actual wavelengths of peak magnitudes of the return spectrum. In some embodiments the process determines wavelength shifts of actual versus expected peak magnitudes. In some embodiments the process instead or in addition compares actual peak magnitudes with expected peak magnitudes. In some embodiments the process instead or in addition determines or compares actual peak widths with expected peak widths. In some embodiments peak widths are determined at predefined magnitudes.

In block 917 the process updates parameters relating to operation of the XRF device. In some embodiments the process updates the parameters based on the analysis of the information of the sensed return spectrum. In some embodiments the parameters include parameters relating to generation of x-rays by the device. In some embodiments the parameters include parameters relating to a length in time of generation of x-rays by the device. In some embodiments the parameters include parameters correlating peak magnitudes at various wavelengths with identification of elements or alloys.

In block 919 the process prepares the XRF device for use utilizing the updated parameters. In some embodiments the process prepares the XRF device for use by opening the shutter.

The process thereafter returns.

Figure 10:
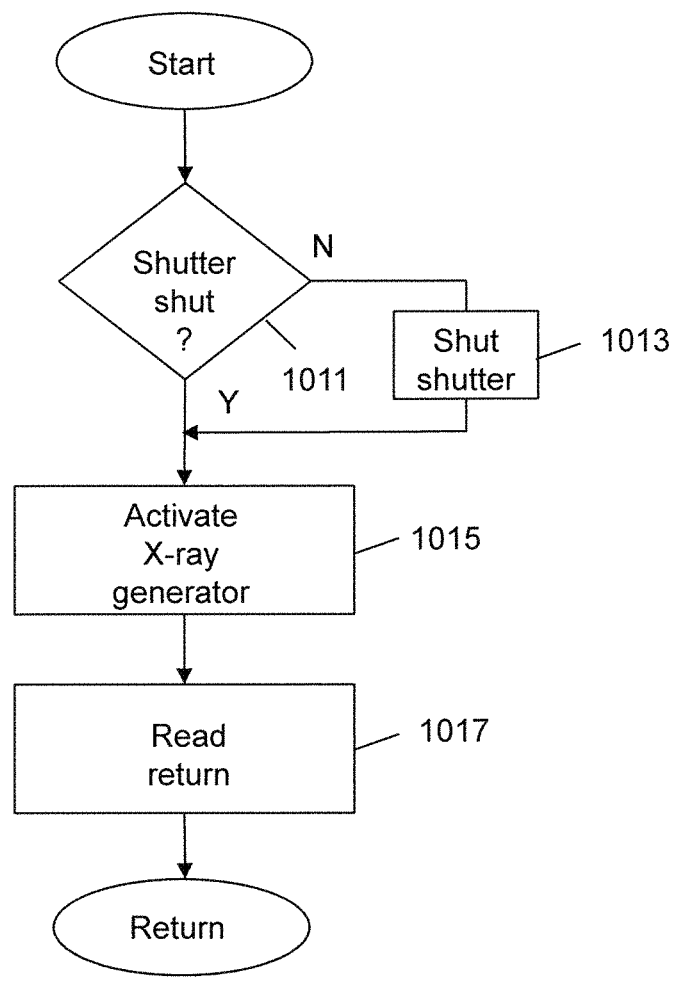
FIG. 10 is a flow diagram of a process of performing a calibration reading in accordance with aspects of the invention.

FIG. 10 is a flow diagram of a process of performing a calibration reading. The process of FIG. 10 may, for example, be performed by the device of FIG. 1, and portions of the process of FIG. 1 may be performed by electronic circuitry of the device of FIG. 1. In some embodiments the electronic circuitry may comprise a processor configured by program instructions. In some embodiments the process of FIG. 10 performs processing of block 913 of the process of FIG. 9.

In block 1011 the process determines if the shutter of the XRF device is in the closed or shut position. In most embodiments the shutter is in the shut position if the shutter blocks a path of x-rays from an x-ray generator of the device to a window of the device. In some embodiments the process determines if the shutter is in the shut position based on a position of a spindle of a motor used to move the shutter. In some embodiments the process determines if the shutter is in the shut position based on a history of commands sent to the motor. In some embodiments the process determines if the shutter is in the shut position by reading information of a sensor indicating position of the shutter.

If the shutter is in the shut position the process continues to block 1013 and shuts the shutter. In some embodiments the process shuts the shutter by commanding activation of a motor coupled to the shutter, with activation of the motor resulting in movement of the shutter.

In block 1015, with the shutter in the shut position, the process activates the x-ray generator of the device. In some embodiments the process activates the x-ray generator for a predetermined period of time. In some embodiments the process activates the x-ray generator until circuitry of the XRF device indicates that the x-ray generator has been activated for a sufficient period of time to obtain a return spectrum signal.

In block 1017 the process reads a return signal from the shutter, or calibration material of the shutter. In some embodiments the return signal is emissions generated by x-rays striking material of the shutter, or calibration material of the shutter.

The process thereafter returns.

Figure 11:
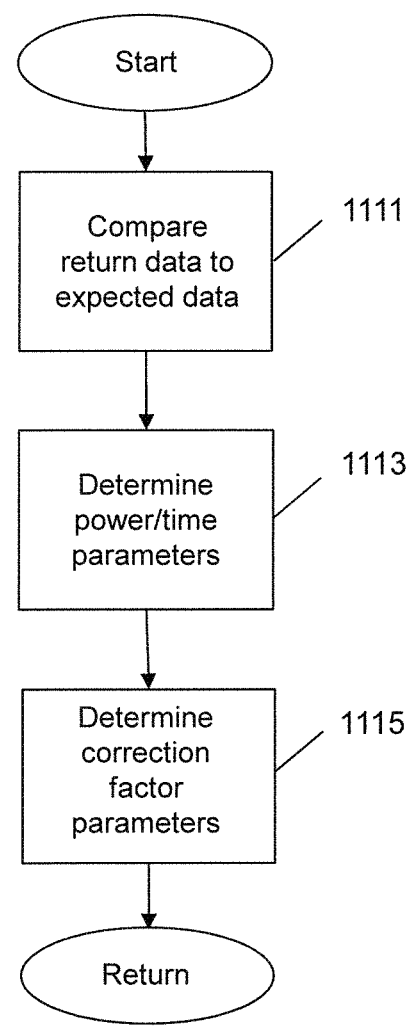
FIG. 11 is a flow diagram of a process of performing a calibration reading in accordance with aspects of the invention.

FIG. 11 is a flow diagram of a process of performing a calibration reading. The process of FIG. 11 may, for example, be performed by the device of FIG. 1, or, for example, by electronic circuitry of the device of FIG. 1, or, for example, by electronic circuitry of the device of FIG. 1 and electronic circuitry of another device in communication with the device of FIG. 1. In some embodiments the electronic circuitry may comprise a processor configured by program instructions. In some embodiments the process of FIG. 10 performs processing of block 915 of the process of FIG. 9.

In block 1111 the process compares return data with expected return data. The return data may include spectrum information, for example indicating amplitude of a return signal at various wavelengths. Similarly, the expected return data may indicate amplitude of an expected return signal at various wavelengths. In some embodiments the process determines differences in magnitudes between actual and expected amplitudes at various wavelengths.

In block 1113 the process determines power/time parameters for x-ray generation. For example, in some embodiments the process may determine a period of time for operation of the x-ray generator of the XRF device based on differences in magnitude between actual and expected amplitudes at various wavelengths. In some embodiments, however, operations of block 1113 are not performed.

In block 1115 the process determines correction factors for use in determining material composition based on return signals. In some embodiments the correction factors indicate a correction to be applied when comparing actual return signals with expected return signals of various materials.

The process thereafter returns.

Although the invention has been discussed with respect to various embodiments, it should be recognized that the invention comprises the novel and non-obvious claims supported by this disclosure.

What is claimed is:

1. A method of calibrating a device, comprising:
generating x-rays from an x-ray generator within a housing;
receiving a return signal emitted by a material struck by the x-rays in a sensor, the material being of a shutter within the housing;
providing data generated by the sensor to electronics connected to the x-ray generator and the sensor;
processing the data in the electronics;
wherein the electronics comprise at least one processor, and the data from the sensor comprises wavelengths of a set of peak magnitudes of a return spectrum, and the at least one processor compares the wavelengths of the set of peak magnitudes of the return spectrum with a set of expected wavelengths of peak magnitudes of a return spectrum, and updates parameters relating to the operation of the x-ray generator and sensor based on the analysis of the comparison of the wavelengths of the set of peak magnitudes of the return spectrum with the set of expected wavelengths of peak magnitudes of the return spectrum, the updated parameters including parameters relating to a length of time of generation of x-rays by the device.

2. The method of claim 1, wherein the material is a calibration material.

3. The method of claim 2, wherein the x-ray generator, calibration material, sensor, and electronics are contained in the housing.

4. The method of claim 3, wherein the shutter occludes at least one window in the housing during calibration.

5. The method of claim 2, wherein the calibration material is a uniform material.

6. The method of claim 2, wherein the calibration material is a laminate.

7. The method of claim 2, wherein the calibration material comprises multi-filament ropes.

8. The method of claim 2, wherein the calibration material comprises a plurality of elements in an epoxy mixture.

9. The method of claim 2, wherein the calibration material comprises a plurality of particles, at least some of the plurality of particles including different elements, in an epoxy mixture.

10. The method of claim 2, wherein the calibration material comprises a plurality of elements in a matrix.

11. The method of claim 2, wherein the calibration material comprises a plurality of particles, at least some of the plurality of particles including different elements, in a matrix.

12. The method of claim 1, wherein the at least one processor updates parameters relating to generation of x-rays by the x-ray generator.

* * * * *